United States Patent
Lindstaedt et al.

(10) Patent No.: US 9,434,667 B2
(45) Date of Patent: Sep. 6, 2016

(54) METHOD FOR ISOLATION OF 1,3-PROPANEDIOL FROM POST-FERMENTATION BROTH OBTAINED BY BIOCONVERSION

(71) Applicant: PROCHIMIA SURFACES SP. Z O.O., Sopot (PL)

(72) Inventors: Agnieszka Lindstaedt, Gdansk (PL); Dariusz Witt, Gdansk (PL); Joanna Puzewicz-Barska, Gdynia (PL); Piotr Barski, Sopot (PL)

(73) Assignee: Prochimia Surfaces SP. Z.o.o., Sopot (PL)

( * ) Notice: Subject to any disclaimer, the term of this patent is extended or adjusted under 35 U.S.C. 154(b) by 0 days.

(21) Appl. No.: 14/431,976

(22) PCT Filed: Sep. 27, 2013

(86) PCT No.: PCT/PL2013/000124
§ 371 (c)(1),
(2) Date: Mar. 27, 2015

(87) PCT Pub. No.: WO2014/051448
PCT Pub. Date: Apr. 3, 2014

(65) Prior Publication Data
US 2015/0259269 A1    Sep. 17, 2015

(30) Foreign Application Priority Data
Sep. 28, 2012 (PL) .......................... 400979

(51) Int. Cl.
| | |
|---|---|
| *C07C 27/26* | (2006.01) |
| *C07C 29/76* | (2006.01) |
| *B01D 11/04* | (2006.01) |
| *C12P 7/18* | (2006.01) |
| *C07C 29/80* | (2006.01) |
| *B01D 11/00* | (2006.01) |

(52) U.S. Cl.
CPC .............. *C07C 29/76* (2013.01); *B01D 11/04* (2013.01); *C07C 29/80* (2013.01); *C12P 7/18* (2013.01); *B01D 2011/007* (2013.01)

(58) Field of Classification Search
CPC ................................ C07C 29/80; C07C 29/76
USPC ........................................................ 568/868
See application file for complete search history.

(56) References Cited

U.S. PATENT DOCUMENTS

| | | | |
|---|---|---|---|
| 5,008,473 | A | 4/1991 | Breitkopf et al. |
| 6,603,048 | B1 | 8/2003 | Corbin et al. |
| 7,056,439 | B2 | 6/2006 | Baniel et al. |
| 2006/0124545 | A1* | 6/2006 | Baniel ................ B01D 11/0446 210/634 |
| 2012/0184783 | A1 | 7/2012 | Barnicki |

FOREIGN PATENT DOCUMENTS

| | | |
|---|---|---|
| CN | 1460671 A | 12/2003 |
| CN | 1907929 A | 2/2007 |
| CN | 101012151 A | 7/2010 |
| CN | 101497556 A | 2/2013 |
| EP | 0261554 A | 8/1991 |
| EP | 1103618 B1 | 7/2006 |
| EP | 1720814 B1 | 2/2012 |

OTHER PUBLICATIONS

International Search Report for App. No. PCT/PL2013/000124 filed Sep. 27, 2013.

* cited by examiner

*Primary Examiner* — Jafar Parsa
(74) *Attorney, Agent, or Firm* — Walker & Jocke

(57) ABSTRACT

A method for isolation of 1,3-propanediol from post-fermentation broth is disclosed. The method generally involves the following steps: (1) biomass removal from post-fermentation broth by one of the following methods: ultrafiltration, filtration, centrifugation or sedimentation; (2) 1,3-propanediol extraction with organic solvent mixture containing 2-butanone with high efficiency performed continuously or stepwise; (3) distillation under vacuum to obtain highly pure target product and (4) organic solvent recovery and recycling the solvent back into the process. The method is useful for recovering valuable 1,3-propanediol from aqueous solutions produced by fermentation.

20 Claims, No Drawings

METHOD FOR ISOLATION OF 1,3-PROPANEDIOL FROM POST-FERMENTATION BROTH OBTAINED BY BIOCONVERSION

TECHNICAL FIELD

The exemplary techniques disclosed herein relate to methods for isolation of 1,3-propanediol from post-fermentation broth obtained by bioconversion.

BACKGROUND 1,3-propanediol is mainly used as a monomer, to build polymer PTT (polytrimethylene terephthalate) used in production of fibers, carpets, textiles for sanitary and medical applications, and as a packaging and/or structural material.

Techniques for extraction of 1,3-propanediol from post-fermentation broth, obtained from a fermentation process have drawbacks and may benefit from improvement.

U.S. Pat. No. 7,056,439 discloses a method for extraction of 1,3-propanediol from fermentation broth with alcohols (pentanol, propanol, hexanol, oleyl alcohol), ketones (4-methyl-2-pentanone), esters (isopropyl acetate, tributyl phosphate), oleic acid, soybean oil, alkanes (n-hexane) and mixtures thereof. This method requires multiple extraction with different solvents and reverse extraction to aqueous phase. Maximum purity of isolated 1,3-propanediol using this method is 95-98.5%.

U.S. Pat. No. 5,008,473 describes a method for isolation of 1,3-propanediol with cyclohexane.

European Patent Application No. 1,720,814 B1 shows a method for isolation of hydrophilic organic compounds, including 1,3-propanediol, with glycol ether at a temperature and then as a result of heating to a higher temperature to obtain an aqueous extract with hydrophilic compound and ether rafinate. The method is based on extraction with ether glycols and a phenomenon specific for them of decreasing the ether solubility in aqueous phase with the increase of temperature. The method discloses also addition of organic solvents in order to further decrease the glycol ethers solubility in aqueous phase during a reverse extraction step to aqueous phase. Among additives some ketones are mentioned. In this method organic solvent is not used alone for extraction per se. This function is fulfilled by glycol ether, that by nature, forces the temperature increase and reverse extraction to aqueous phase. The whole solution thus constitutes the concentration of 1,3-propanediol in aqueous phase, as in U.S. Pat. No. 7,056,439.

U.S. Patent Publication 20120184783 discloses a process for purification of particular diols, including 1,3-propanediol, from diols mixture by extraction with an organic solvent or a mixture of organic solvents. A proper selection of solvent mixture allows recovery of a selected diol group (comprising three, four and five carbon atoms), from the starting mixture, where content of water is max. 50 wt. %.

Chinese Patent Application No. 101012151A describes a method of 1,3-propanediol isolation from post-fermentation broth containing trimethylene glycol in the range of (30-700 g/L) comprising an initial saturation with inorganic salts (10-100%) and organic solvent addition for extraction.

Chinese Patent Application No. 1907929 discloses a method of isolation of 1,3-propanediol from fermentation broth containing trimethylene glycol by extraction combined with chemical reaction. The recovery of 1,3-propanediol is made after hydrolysis and distillation.

A similar recovery technique is presented by Malinowski et al. (Biotechnol. Prog., 16: 76-79, 2000). This extraction is based on isolation of 1,3-propanediol by extraction with aldehydes, as reactants, converting 1,3-propanediol into alkyl dioxane and the product is next extracted with organic solvents (toluene, o-xylene, ethylbenzene).

A process of 1,3-propanediol extraction from post-fermentation broth with mixture of ethyl acetate and ethanol is known from Separation Science and Technology, 45: 541-547, 2010.

1,3-propanediol can also be recovered by continuous liquid-liquid extraction (Biotechnol. Tech., 13: 127-130, 1999).

Chinese Patent Application No. 1460671A discloses a step of thermal concentration for reduction of volume of the post-fermentation broth (containing the product) and biomass removal step by precipitation with organic solvent. Liquid-liquid extraction and aqueous/organic phase mixing are not mentioned. Mixing is performed only during biomass washing after precipitation. Methyl-ethyl ketone is added, as a precipitating agent, only to remove the biomass, but not as the extractant. This is evidenced by absence of phase distribution (aqueous/organic) and extraction of the supernatant was not performed.

Chinese Patent Application No. 1460671A describes a process for distillation of a mixture of water (from post-fermentation broth) and an organic solvent (used for precipitation of biomass). The described approach is lacking in the critical liquid-liquid extraction process.

European Patent Application No. 0261554 A discloses extraction of 1,3-propanediol with cyclohexane.

European Patent Application No. 1103618B1 is based on a known method of ion exchange chromatography, where 1,3-propanediol is isolated using a cationic resin, and in a next step a column of activated carbon and a weak basic anionic resin or cationic resin and strong basic anionic resin.

U.S. Pat. No. 6,603,048 discloses a method of isolation of 1,3-propanediol from post-fermentation broth, which comprises 1,3-propanediol, and other fermentation co-products, (inter alia, glycerol), using molecular sieves, which are zeolites. The process is an example of industrial use of 1,3-propanediol recovery method from the post-fermentation broth. Despite its industrial use, the method uses an expensive separation medium and separation of products on a semi-continuous basis that generates additional capital and production expenses.

Chinese Patent Application No. 101497556A discloses a solid super acidic catalyst method as a method for isolation of 1,3-propanediol followed by aldol condensation reaction, and rectification.

SUMMARY

Exemplary embodiments relate to a method of continuous liquid-liquid extraction from post-fermentation broth (after biomass removal) with 2-butanone, with no use of catalyst reaction and aldol reaction.

DETAILED DESCRIPTION

Exemplary method embodiments will be described. Various modifications, adaptations or variations of the exemplary embodiments described herein may become apparent to those skilled in the art as such are disclosed. It will be understood that all such modifications, adaptations or variations that rely upon the teachings hereof, and through which these teachings have advanced the art, are considered to be within the scope and spirit of the disclosure presented herein.

The methods and compositions of the exemplary embodiments may suitably comprise, consist of, or consist essentially of the components, ingredients, elements, steps and process delineations described herein. The embodiments illustratively disclosed herein suitably may be practiced in the absence of any element, process step, or ingredient which is not specifically disclosed herein.

Unless otherwise stated, all percentages, parts, and ratios expressed herein are based upon weight of the total compositions.

The headings provided herein serve to illustrate, but not to limit the teachings herein in any way or manner.

As used herein "bioconversion" is a synonym of any fermentation process leading to enzymatic/biochemical production of 1,3-propanediol.

An object of an exemplary embodiment is a method for isolation of 1,3-propanediol from the post-fermentation broth comprising 1,3-propanediol extraction using a mixture of organic solvents, characterized in that 1,3-propanediol is isolated, after previous biomass removal from post-fermentation broth, with 2-butanone that is present in the organic solvent mixture. The method is carried out continuously or stepwise and the organic solvent used in the extraction method is used repeatedly. The content of 2-butanone in organic solvents mixture is minimum 10%, and the volume ratio of post-fermentation broth, containing 1,3-propanediol, to the mixture of organic solvents is minimum 1:3.

After previous biomass removal, the exemplary method includes isolation of 1,3-propanediol is without salting out or concentration of post-fermentation broth. The exemplary method is also characterized in that isolation of 1,3-propanediol using an organic solvent mixture, is followed by distillation under vacuum to obtain highly pure 1,3-propanediol. Biomass is removed from the post-fermentation broth comprising 1,3-propanediol in an exemplary embodiment by: ultrafiltration, filtration, centrifugation or sedimentation, and then the extraction of 1,3-propanediol with organic solvent mixture is carried out.

The exemplary method of 1,3-propanediol recovery from post-fermentation broth is based on continuous or stepwise 1,3-propanediol extraction with an organic solvent, such as but not limited to 2-butanone.

An advantage of the exemplary method is the increased ratio of recovery of 1,3-propanediol from post-fermentation broth obtained from a fermentation process leading to production of 1,3-propanediol, as a main product. As the source of carbon, there can be employed glycerol or carbohydrates.

The post-fermentation broth intended for isolation may comprise glycerol residues, 1,3-propanediol, impurities such as organic acids, including mainly: acetic acid, butyric acid, and carbohydrates (i.e mainly glucose, fructose, dextrose, xylose, arabinose, water-soluble starch fraction and cellulose residues). The presence of carbohydrates in the post-fermentation broth does not affect the efficiency of 1,3-propanediol extraction with 2-butanone.

The exemplary method achieves a desired concentration of 1,3-propanediol in the extract with high efficiency due to a possibility of recycling organic solvent used in the extraction process (either continuous or stepwise). During the exemplary methods of extraction of 1,3-propanediol from post-fermentation broth, no emulsion is formed at the interface between the phases, wherein what usually happens in the case of solvents used previously (ethyl acetate, n-hexane, toluene, 4-methyl-2-pentanone) and considerably restricts, if not eliminates the use of such organic solvent in an industrial process.

The exemplary isolation is performed directly from the post-fermentation broth without any additional procedures, such as water evaporation (concentration) or inorganic salt addition (as in the method of Chinese Patent Application No. 101012151A). Only biomass removal from post-fermentation broth is required. The exemplary isolation method of 1,3-propanediol from the post-fermentation broth requires low energy input. The obtained extract is solely further distilled under vacuum to produce a final product with 99.90% purity. The exemplary method is short (two steps), inexpensive and based on unique properties of an organic solvent that is useful in such a method. Due to limitation of the number of isolation process steps and as a consequence, costs of 1,3-propanediol recovery from post-fermentation broth, the exemplary method may bemore attractive than known methods.

An exemplary embodiment of the method has no concentration or precipitation steps, and organic solvent is used for liquid-liquid extraction and not for biomass precipitation.

The method for isolation of 1,3-propanediol described in U.S. Pat. No. 5,008,473 is not suitable for mixtures obtained in biotechnological processes and containing glycerol.

The method for isolation of diols from post-fermentation broth with glycerol content of less than 5 wt. % or selective isolation of 1,3-propanediol described in U.S. Patent Publication 20120184783 is not effective. Additionally the method in U.S. Patent Publication 20120184783 fails to use four-carbon ketones (C4) such as 2-butanone.

Chinese Patent Application No. 1907929 disclosed method of isolation of 1,3-propanediol from fermentation broth is a costly and multistage process which reduces efficiency thereof and has negative impact on its profitability.

Chinese Patent Application No. 101012151A does not describe any application of more than three-carbon ketones (C3) and the method concerns specific fermentation broth with trimetylene glycol and comprises a technically inconvenient and expensive step of inorganic salt addition.

The exemplary method disclosed herein, in contrast to the methods disclosed in Chinese Patent Application No. 1460671A, the extracted substance (1,3-propanediol) in the liquid-liquid extraction becomes distributed between a primary solution (post-fermentation broth) and a secondary solution (organic solvent—methyl-ethyl ketone, with which the key compound is extracted). As a result, a rafinate is obtained (a solution basically without 1,3-propanediol) and an extract, containing 1,3-propanediol. Solely the extract (not all the aqueous phase—supernatant from steps 2 and 3 as in CN1460671A) is further purified (eg. subject to distillation) to acquire pure final product and solvent (extractant).

According to the exemplary embodiments, at the step of solvent recovery and final product purification, due to efficient counter-current extraction, the water content is minimized to 12% of water solubilized in methyl-ethyl ketone because of mixing during liquid-liquid extraction process.

The exemplary methods concerns 1,3-propanediol isolation in continuous liquid-liquid extraction from post-fermentation broth (after biomass removal) by means of 2-butanone and final product distillation, rather than the disclosure in European Patent Application No. 0261554 describing using cyclohexane.

The method of European Patent Application No. 1103618B1 differs from the exemplary methods hereof as 1,3-propanediol is isolated in the continuous liquid-liquid extraction from post-fermentation broth (after biomass removal) by means of 2-butanone and final product distillation, rather than using ion exchange chromatography.

EXAMPLES

The useful aspects of exemplary embodiments are demonstrated in the following examples. The following examples are intended to show the principles and advantages of the approaches are disclosed herein, but are not to be viewed as limiting.

Example 1

Upon biomass removal by centrifugation the post-fermentation broth containing 1,3-propanediol (27.6 g/L, 100 mL) and 2-butanone (200 mL) were placed in the apparatus for continuous extraction (Soxhlet extractor for liquid-liquid extraction with organic solvent lighter than water). 2-butanone (150 mL) was heated in a round-bottom flask for 1 h. Next the 1,3-propanediol content in organic and aqueous phases were determined. The continuous extraction of 1,3-propanediol was repeated 10 times for each fresh portion of 100 mL of post-fermentation mixture of 1,3-propanediol (27.6 g/L) with the same amount of solvent (no replacement). Average yield of the extraction process was 91%. The resulting post-fermentation mixture was subsequently distilled under vacuum and the final product, 1,3-propanediol, was obtained with 99.90% purity. Depending on the given pressure (9-18 mmHg) the boiling point of 1,3-propanediol was varying in the range of 94-120° C.

Example 2

Upon biomass removal by centrifugation the post-fermentation broth containing 1,3-propanediol (35 g/L, 100 mL) and 2-butanone (200 mL) were placed in the apparatus for liquid-liquid continuous extraction (Soxhlet extractor for liquid-liquid extraction with organic solvent lighter than water). 2-butanone (150 mL) was heated in a round-bottom flask for 1 h. The 1,3-propanediol content in organic and aqueous phases were determined. The continuous extraction of 1,3-propanediol was repeated 10 times for each fresh portion of 100 mL of post-fermentation broth of 1,3-propanediol (27.6 g/L) with the same amount of solvent (no replacement). Average yield of the extraction process was 84%. The extract was subsequently distilled under vacuum and the final product, 1,3-propanediol, was obtained with 99.90% purity. Depending on the pressure (9-18 mmHg) the boiling point of 1,3-propanediol was varying in the range of 94-120° C.

Example 3

Upon biomass removal by centrifugation the post-fermentation broth containing 1,3-propanediol (60 g/L, 100 mL) and 2-butanone (200 mL) were placed in the apparatus for liquid-liquid continuous extraction (Soxhlet extractor for liquid-liquid extraction with organic solvent lighter than water). 2-butanone (150 mL) was heated in a round-bottom flask for 1 h. The 1,3-propanediol content in organic and aqueous phases were determined. The continuous extraction of 1,3-propanediol was repeated 10 times for each fresh portion of 100 mL of post-fermentation mixture of 1,3-propanediol (27.6 g/L) with the same amount of solvent (no replacement). Average yield of the extraction process was 73%. The extract was subsequently distilled under vacuum and the final product, 1,3-propanediol, was obtained with 99.90% purity. Depending on the pressure (9-18 mmHg) the boiling point of 1,3-propanediol was varying in the range of 94-120° C.

Example 4

Upon biomass removal by centrifugation the post-fermentation broth containing 1,3-propanediol (35 g/L, 100 mL) and 2-butanone (200 mL) were placed in the apparatus for liquid-liquid continuous extraction (Soxhlet extractor for liquid-liquid extraction with organic solvent lighter than water). 2-butanone (150 mL) was heated in a round-bottom flask for 1.5 h. The 1,3-propanediol content in organic and aqueous phases were determined. The continuous extraction of 1,3-propanediol was repeated 10 times for each fresh portion of 100 mL of post-fermentation mixture of 1,3-propanediol (27.6 g/L) with the same amount of solvent (no replacement). Average yield of the extraction process was 90%. The extract was subsequently distilled under vacuum and the final product, 1,3-propanediol, was obtained with 99.90% purity. Depending on the pressure (9-18 mmHg) the 1,3-propanediol boiling point was varying in the range of 94-120° C.

Example 5

Upon biomass removal by centrifugation the post-fermentation broth containing 1,3-propanediol (60 g/L, 100 mL) and 2-butanone (200 mL) were placed in the apparatus for liquid-liquid continuous extraction (Soxhlet extractor for liquid-liquid extraction with organic solvent lighter than water). 2-butanone (150 mL) was heated in a round-bottom flask for 2 h. The 1,3-propanediol content in organic and aqueous phases were determined. The continuous extraction of 1,3-propanediol was repeated 10 times for each fresh portion of 100 mL of post-fermentation mixture of 1,3-propanediol (27.6 g/L) with the same amount of solvent (no replacement). Average yield of the extraction process was 92%. The extract was subsequently distilled under vacuum and the final product, 1,3-propanediol, was obtained with 99.90% purity. Depending on the pressure (9-18 mmHg) the 1,3-propanediol boiling point was varying in the range of 94-120° C.

Example 6

The results of lab-scale experiments were verified in pilot scale testing using extraction columns (Karr reciprocating column). Upon biomass removal by centrifugation the post-fermentation broth containing 1,3-propanediol (27 g/L) and 2-butanone were placed in separated containers and pumped at the ratio of 1:7 (post-fermentation broth comprising 1,3-propanediol:organic solvent, v/v) into Karr reciprocating column in countercurrent flow. Column temperature range was 20-40° C. The process was carried out continuously. Average yield of extraction process was 80%.

Example 7

Upon biomass removal by centrifugation the post-fermentation broth containing 1,3-propanediol (27 g/L) and 2-butanone were placed in separated containers and pumped at the ratio of 1:10 (post-fermentation broth containing 1,3-propanediol:organic solvent, v/v) into Karr reciprocating column in countercurrent flow. Column temperature range was 20-40° C. The process was carried out continuously. Average yield of extraction process was 85%.

Example 8

Upon biomass removal by centrifugation the post-fermentation broth containing 1,3-propanediol (27 g/L) and 2-butanone were placed in separated containers and pumped at the ratio of 1:15 (post-fermentation broth containing 1,3-propanediol:organic solvent, v/v) into Karr reciprocating column in countercurrent flow. Column temperature range was 20-40° C. The process was carried out continuously. Average yield of extraction process was 93%.

Example 9

Upon biomass removal by centrifugation the post-fermentation broth containing 1,3-propanediol (27 g/L) and 2-butanone were placed in separated containers and pumped at the ratio of 1:7 (post-fermentation broth containing 1,3-propanediol:organic solvent, v/v) into Scheibel extraction column in countercurrent flow. Column temperature range was 20-40° C. The process was carried out continuously. Average yield of extraction process was 77%.

Example 10

Upon biomass removal by centrifugation the post-fermentation broth containing 1,3-propanediol (27 g/L) and 2-butanone were placed in separated containers and pumped at the ratio of 1:10 (post-fermentation broth containing 1,3-propanediol:organic solvent, v/v) into Scheibel extraction column in countercurrent flow. Column temperature range was 20-40° C. The process was carried out continuously. Average yield of extraction process was 88%.

Based on the laboratory scale experiments it has been demonstrated that the time of 1,3-propanediol extraction process with organic solvent should be accordingly prolonged if the concentration of 1,3-propanediol in post-fermentation broth is increased to obtain similar process efficiency using the same amount of organic solvent.

With pilot scale experiments the process is controlled by the volume ratio of post-fermentation broth (containing 1,3-propanediol) to organic solvent.

Thus the exemplary embodiments achieve improved capabilities, eliminate difficulties encountered in the use of prior methods, and attain the useful results described herein.

In the foregoing description certain terms have been used for brevity, clarity and understanding. However, no unnecessary limitations are to be implied therefrom because such terms are used for descriptive purposes and are intended to be broadly construed. Moreover, the descriptions and illustrations herein are by way of examples and the invention us not limited to the features shown and described.

It should be understood that features and/or relationships associated with one embodiment can be combined with features and/or relationships from another embodiment. That is, various features and/or relationships from various embodiments can be combined in further embodiments. The inventive scope of the disclosure is not only limited to only the embodiments shown or described herein.

Having described the features, discoveries and principles of the exemplary embodiments, the manner in which they are carried out and the advantages and useful results attained, the new and useful methods, elements, arrangements, combinations, operations, methods, processes and relationships are set forth in the appended claims.

We claim:

1. A method for isolation of 1,3-propanediol from the post-fermentation broth comprising:
    a) removing biomass from post-fermentation broth; and
    b) extracting 1,3-propanediol using a mixture of organic solvents, wherein the mixture contains 2-butanone.

2. The method according to claim 1,
repeating step (b) a plurality of times using the same organic solvent mixture.

3. The method according to claim 1,
wherein the said method is carried out stepwise and organic solvent used in the extraction process is used repeatedly.

4. The method according to claim 1,
wherein in step (b) the organic solvent mixture comprises at least 10% (v/v) 2-butanone.

5. The method according to claim 1,
wherein the volume ratio of the post-fermentation broth, comprising 1,3-propanediol after biomass removal in step (a) to the organic solvent mixture in step (b) is at a minimum 1:3.

6. The method according to claim 1,
wherein in step (a) the biomass removal is conducted without salting out or concentrating the post-fermentation broth.

7. The method according to claim 1, and further comprising step (c) subsequent to step (b) distilling the extracted 1,3-propanediol under vacuum to obtain purified 1,3-propanediol.

8. The method according to claim 7, wherein in step (c) the 1,3-propanediol is distilled to at least 99.90% purity.

9. The method according to claim 1,
wherein in (a) removing the biomass from post-fermentation broth is carried out using at least one of the following methods: ultrafiltration, filtration, centrifugation and sedimentation.

10. The method according to claim 2,
wherein in step (b) the organic solvent mixture comprises at least 10% (v/v) 2-butanone.

11. The method according to claim 2,
wherein the volume ratio of the post-fermentation broth, comprising 1,3-propanediol after biomass removal in step (a) to the organic solvent mixture in step (b) is at a minimum 1:3.

12. The method according to claim 2,
wherein in step (a) the biomass removal is conducted without salting out or concentrating the post-fermentation broth.

13. The method according to claim 2, and further comprising step (c) subsequent to step (b) distilling the extracted 1,3-propanediol under vacuum to obtain purified 1,3-propanediol.

14. The method according to claim 2,
wherein in (a) removing the biomass from post-fermentation broth is carried out using at least one of the following methods: ultrafiltration, filtration, centrifugation and sedimentation.

15. The method according to claim 3,
wherein in step (b) the organic solvent mixture comprises at least 10% (v/v) 2-butanone.

16. The method according to claim 3,
wherein the volume ratio of the post-fermentation broth, comprising 1,3-propanediol after biomass removal in step (a) to the and organic solvent mixture in step (b) is at a minimum 1:3.

17. The method according to claim 3,
wherein in step (a) the biomass removal is conducted without salting out or concentrating the post-fermentation broth.

18. The method according to claim 3, and further comprising step (c) subsequent to step (b) distilling the extracted 1,3-propanediol under vacuum to obtain purified 1,3-propanediol.

19. A method for isolation of 1,3-propanediol from the post-fermentation broth comprising:
   a) removing biomass from post-fermentation broth; and
   b) extracting, without using back extraction, 1,3-propanediol using a mixture of organic solvents, wherein the mixture contains 2-butanone.

20. A method for isolation of 1,3-propanediol from the post-fermentation broth comprising:
   a) removing biomass from post-fermentation broth;
   b) extracting, without using back extraction, 1,3-propanediol using a mixture of organic solvents, wherein the mixture contains 2-butanone,
   c) subsequent to step (b) distilling the extracted 1,3-propanediol under vacuum to obtain purified 1,3-propanediol;
      wherein in step (c) the 1,3-propanediol is distilled to at least 99.90% purity.

* * * * *